(12) United States Patent
Aebi et al.

(10) Patent No.: US 10,278,748 B2
(45) Date of Patent: May 7, 2019

(54) IMPLANT FOR STABILIZING FRACTURED OR NON-FRACTURED BONES, USE OF AN IMPLANT AND METHOD FOR STABILIZING FRACTURED OR NON-FRACTURED BONES

(71) Applicant: HYPREVENTION, Pessac (FR)

(72) Inventors: Max Aebi, Bern (CH); Marek Szpalski, Brussels (BE); Robert Gunzburg, Berchem (BE); Cécile Vienney, Bordeaux (FR)

(73) Assignee: Hyprevention, Pessac (FR)

( * ) Notice: Subject to any disclaimer, the term of this patent is extended or adjusted under 35 U.S.C. 154(b) by 0 days.

(21) Appl. No.: 15/524,035

(22) PCT Filed: Oct. 15, 2015

(86) PCT No.: PCT/EP2015/073845
§ 371 (c)(1),
(2) Date: May 3, 2017

(87) PCT Pub. No.: WO2016/071089
PCT Pub. Date: May 12, 2016

(65) Prior Publication Data
US 2017/0258503 A1    Sep. 14, 2017

(30) Foreign Application Priority Data
Nov. 4, 2014 (EP) .................... 14306759

(51) Int. Cl.
*A61B 17/70* (2006.01)
*A61B 17/72* (2006.01)
(Continued)

(52) U.S. Cl.
CPC ........ *A61B 17/725* (2013.01); *A61B 17/7098* (2013.01); *A61B 17/846* (2013.01);
(Continued)

(58) Field of Classification Search
CPC . A61B 17/8811; A61B 17/746; A61B 17/725; A61B 17/7098; A61B 17/0401;
(Continued)

(56) References Cited

U.S. PATENT DOCUMENTS 5,743,912 A  * 4/1998 Lahille ................. A61B 17/742
                                                    606/290
8,574,273 B2 * 11/2013 Russell ............... A61B 17/0401
                                                    606/304
(Continued)

FOREIGN PATENT DOCUMENTS

CN      103 479 420 A     1/2014
JP      H09-149906 A      6/1997
(Continued)

OTHER PUBLICATIONS

European Search Report Corresponding to 14306759.3 dated Apr. 22, 2015.
(Continued)

*Primary Examiner* — Pedro Philogene
(74) *Attorney, Agent, or Firm* — Davis & Bujold PLLC; Michael J. Bujold

(57) ABSTRACT

A bone implant (1) for stabilizing fractured or non-fractured bones comprises an implant body (2), preferably a cylindrical body, extending along a longitudinal axis (3) from a front side (4) to an end side (5). The implant has an implant width (6) extending perpendicularly to the longitudinal axis (3), and a length of the implant body (2) along the longitudinal axis (3) is at least 5 times the width (6) of the implant. The implant body (2) has an outer surface, being at least divided into a first surface (7) and a second surface (8. The first surface (7) comprises an anchorage area (9) which extends at least partially over the outer surface, preferably maximum over half of the outer surface.

12 Claims, 7 Drawing Sheets

(51) Int. Cl.
*A61B 17/84* (2006.01)
*A61B 17/86* (2006.01)

(52) U.S. Cl.
CPC .......... *A61B 17/864* (2013.01); *A61B 17/863* (2013.01); *A61B 17/8635* (2013.01); *A61B 17/8645* (2013.01); *A61B 2017/8655* (2013.01)

(58) Field of Classification Search
CPC ..... A61B 17/742; A61B 17/72; A61B 17/864; A61B 17/866; A61B 2017/0458; A61B 2017/0427; A61B 2017/0412; A61B 2017/0414
USPC .................. 606/62–67, 279, 286, 300–328
See application file for complete search history.

(56) References Cited

U.S. PATENT DOCUMENTS

| | | | | |
|---|---|---|---|---|
| 9,427,268 | B2* | 8/2016 | Ye | ........................... A61B 17/74 |
| 2003/0083662 | A1* | 5/2003 | Middleton | ......... A61B 17/0401 606/323 |
| 2004/0267265 | A1 | 12/2004 | Kyle | |
| 2009/0157078 | A1 | 6/2009 | Mikol | |
| 2010/0030135 | A1* | 2/2010 | Mitchell | ............ A61B 17/7098 604/48 |
| 2012/0123415 | A1 | 5/2012 | Vienney et al. | |
| 2012/0123481 | A1* | 5/2012 | Lin | .................... A61B 17/7032 606/279 |

FOREIGN PATENT DOCUMENTS

| | | |
|---|---|---|
| WO | 2012/066236 A1 | 5/2012 |
| WO | 2012/142032 A1 | 10/2012 |
| WO | 2013/079753 A1 | 6/2013 |
| WO | 2014/149746 A1 | 9/2014 |

OTHER PUBLICATIONS

International Search Report Corresponding to PCT/EP2015/073845 dated Dec. 14, 2015.
Written Opinion Corresponding to PCT/EP2015/073845 dated Dec. 14, 2015.

* cited by examiner

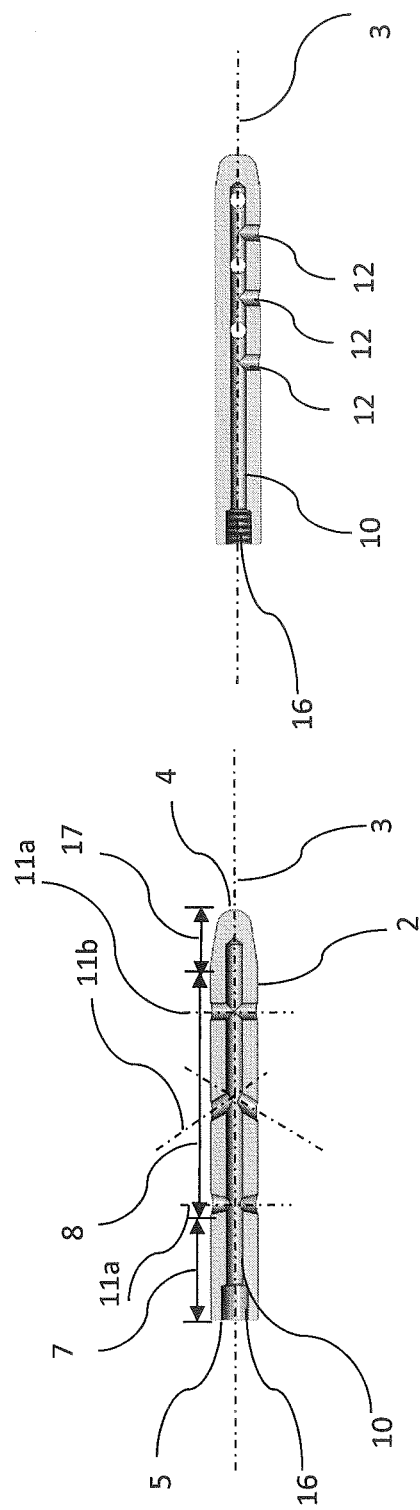

IMPLANT FOR STABILIZING FRACTURED OR NON-FRACTURED BONES, USE OF AN IMPLANT AND METHOD FOR STABILIZING FRACTURED OR NON-FRACTURED BONES

The invention relates to a bone implant, the use of an implant and a method of stabilizing a fractured or non-fractured bone according to the independent claims.

BACKGROUND OF THE INVENTION

Bone implants are widely used for stabilizing fractured bones.

US 2009/0157078 for example discloses a cannulated screw for repairing defects in the humerus or the femur. Part of the screw does not contain a thread but holes through which cement may be introduced into a void into the bone. This device comprises a screw head on one side of the implant which requires the screw to partly extend outside the bone. The other end of the implant is threaded so that the screw is only fixed in case the thread can be fixed inside the bone on the side opposite of the screw head. Such an implant is limited in its applications.

WO 2012/142032 discloses a method and a device for bone preparation. The device comprises an insertion structure with perforations through which a fluid may be introduced into the bone. The device may be used for internal fixation of fractions or can be implemented into possibly weak and/or cancerous bone. The fluid may be bone cement. The implant part of the device is fixed on the outside of the bone and is therefore very complicated. Furthermore, several implants are used in one bone, which weakens the bone tissue due to the number of introduction channels.

WO 2012/066236 is directed to a device combining two intersecting implants for preventive or curative treatment of fractures of the femur. The intersecting implants are fixed relative to each other and thereby prevent any movement of the implants. Such a device can only be applied in bones that allow for intersecting implants.

SUMMARY OF THE INVENTION

It is therefore an object of the present invention to avoid the drawbacks of the prior art and to create a bone implant, the use of a bone implant and a method for stabilizing a fractured or non-fractured bone which can be versatilely used in different bones of the human body and allows for a stable positioning inside the bone.

The object is accomplished by a bone implant for stabilizing fractured or non-fractured bones comprising an implant body which preferably is a cylindrical body. The implant body extends along a longitudinal axis from a front side to an end side. The implant body has an implant width expending perpendicularly to the longitudinal axis, wherein a length of the implant body along the longitudinal axis is at least five times the implant width. The implant body has an outer surface which is at least divided into a first surface and a second surface wherein the first surface consists of an anchorage area which extends at least partially over the outer surface, preferably maximum over half of the outer surface.

The anchorage area according to the invention comprises a surface that improves the fixation of the implant when implanted in a bone. The bone tissue can more easily grow into the implant and the anchorage of the implant in the bone is improved.

Such an implant is easily introduced and fixed inside a bone, especially a vertebra. The anchorage area preferably is located at the proximal end of the implant when implanted into a bone.

The implant body preferably has a constant implant width at least across the first surface and the second surface. Furthermore the implant does not comprise a widening on the proximal end like for example a screw head. Hence, preferably the implant width is constant over at least the first and the second surface, while the implant width in other areas only may be smaller.

The first surface and the second surface respectively preferably extend along the longitudinal axis and 360° around the longitudinal axis.

The implant can comprise a bore extending along the longitudinal axis or parallel to the longitudinal axis having at least one, preferably two openings at the front side and/or at the end side.

A bore inside the bone implant leads to a lighter implant and in case of two openings the possibility of introduction of fluids into the bone.

The length of the bone implant can be in a range from 10 mm to 250 mm.

The specific bone implant can be used for different bones and still has a length needed for stabilizing the respective bone.

The width of the bone can be in a range from 5 mm (for ribs) to 50 mm (for femoral diaphysis) or 80 mm (for humeral head). The width of the bone implant can be in a range from 2 mm to 10 mm.

Such a bone implant can easily be introduced into a bone without destroying further bone tissue and nevertheless delivers enough stability to serve its purpose of stabilizing the bone.

The outer surface, preferably the second surface, can comprise holes having a wall around a hole axis.

The bone implant having holes on the outer surface or second surface respectively on the one hand leads to the possibility of bone tissue growing into the holes and thereby improving positioning of the implant and in case of bone implant having a bore leading to the possibility of directing fluid into the bone tissue around the implant, where holes are located.

The fluid preferably is bone cement, such as PMMA bone cement, bio-resorbable bone cement or any other product allowing implant fixation in a bone.

The holes can have a diameter of 0.2 mm to 5 mm on the outer surface or the second surface respectively.

Through such a hole bone tissue can quickly grow in and fluid, such as bone cement, can easily be introduced into the bone.

The walls of the holes can have a cylindrical, preferably a conical shape.

Cylindrical holes are easy to manufacture and thereby lower manufacturing costs and the conical shape optimizes the distribution of the fluid that is introduced into the bone through the bone implant.

The implant can comprise a first set of holes, wherein the hole axis of the first set of holes is arranged substantially perpendicular to the longitudinal axis.

A set of holes can comprise one or more holes.

A hole with a hole axis arranged perpendicular to the longitudinal axis leads to the distribution of fluid through the hole radially away from the implant and thus the bone cement reaches as far as possible.

The implant can comprise a second set of holes, wherein the hole axis of the second set of holes is inclined relative to the longitudinal axis, preferably inclined as an angle greater than 90° while smaller than 150° relative to the longitudinal axis.

An inclined hole axis enables the distribution of a fluid to a specific point inside the bone when the implant is placed inside the bone.

The implant can comprise a third set of holes, wherein the hole axis of the third set of holes is inclined relative to the longitudinal axis at an angle different from the second set of holes, preferably inclined at an angle smaller than 90° while larger than 30° relative to the longitudinal axis.

An inclined hole axis enables the distribution of a fluid inside the bone to a specific area when the implant is already inside the bone. Furthermore, inclined holes enable the introduction of bone cement even in sensitive areas of nerves, since it is possible to direct the flow of the cement into specific areas.

Especially a combination of the first, second and third set of holes enables the direction of fluid from inside the implant to specific areas of the bone relative to the implant.

The holes can be distributed substantially equal in an area of 360° around the longitudinal axis of the outer surface or the second surface and preferably distributed in rows along the longitudinal axis such that a distance between neighbouring holes in a row is substantially the same.

Such an arrangement allows for an optimised distribution of fluid and a uniform distribution of tissue growing into the implant.

The holes can be located in an area from 180° to 270° around a longitudinal axis on the outer surface or the second surface and preferably distributed in rows along the longitudinal axis such that the distance between neighbouring holes and a row is substantially the same.

The arrangement of the holes in an area from 180° to 270° around the longitudinal axis leads to the possibility of directing fluid through the implant only to a part of the bone, where the fluid is needed.

A first hole of a first row and a first hole of a second neighbouring row can have a different distance to the front side, preferably the difference in the distance is equal to half the distance of two neighbouring holes in a row.

Such a distribution of neighbouring holes of neighbouring rows leads to an optimised distribution of fluid being introduced through the implant into the bone.

The distribution of holes is preferably chosen such that the stability of the implant is not, or not significantly compromised and nevertheless the distribution of fluid is optimal for the specific situation. In spine, the holes will be placed in the distal part of the implant which is implanted in the vertebral body, and the holes will be arranged such that cement is injectable at 270 to 300° around the longitudinal axis, not on the side of an upper endplate to avoid leakage in case of endplate fracture.

In the humerus application, the holes are placed all along the implant, at 360° around the longitudinal axis, to allow a 360° cement flow. This allows a good implant fixation, a bone reinforcement and to full fill tumour if applicable.

The anchorage area can comprise means for improving the fixation of the implant within a bone, preferably a surface structure and/or a roughness and/or recesses.

The surface structure can be grooves, a thread or a ring shaped structure, while the thread or groove pitches or ring structures can be square, symmetrically triangular or asymmetrically triangular. Alternatively or additionally, the surface structure can comprise recesses that are straight, helicoidal or comprise crossed or diamond shaped pitches. A recess in the anchorage area can be from 0.5 mm to 3 mm deep.

All depth values according to this invention are measured from top to bottom. Of course statistical variations can occur.

A surface structure improves the anchorage of the implant.

The roughness can vary from 1 micrometer to 0.5 mm.

The anchorage area can comprise a surface structure in form of grooves, preferably 6 or 8 grooves, distributed substantially equally around the longitudinal axis, extending coaxially along the longitudinal axis.

The grooves can have the same shape and/or height as the recesses and surface structures being a thread or ring shaped.

The use of surface structures in form of grooves improves the anchorage of the implant and therefore leads to a more durable and safer implant.

The anchorage area can comprise a surface structure in form of a thread or ring shaped grooves. Such an anchorage area improves the fixation of the implant inside the bone.

A cross section of the grooves can be U-shaped, V-shaped or square. By means of the grooves, the surface contact between the bone and the implant is increased and stress concentration on the bone is limited. It also allows implant stabilisation in rotation before the cement injection, which is for example important for spinal implants where the injection holes have to be oriented. After cement injection the implant stabilisation is done by the cement e.g. stabilisation of the implant in rotation and translation.

The implant can comprise a fixation connector allowing holding of the implant during introduction into a bone.

The fixation connector can for example be a thread by means of which the bone implant is connected to a tool. Preferably the fixation connector is a thread on the inside of the bore of the bone implant, while the inner thread preferably has a wider diameter than the rest of the bore to improve an easy introduction of a tool. By means of such an inner thread, the outer surface can be optimized for fixation of the implant inside the bone.

Furthermore, the fluid can be introducible through the tool and the implant when connected by the fixation connector. This leads to any easy handling of the implant when introducing and fixing the implant.

The outer surface can comprise a third surface having an at least partially conical shape. Such a third surface is arranged opposite of the anchorage surface and leads to the possibility of easier introducing the bone implant into the bone.

The implant can be made from any implantable material, such as PEEK, titanium, stainless steel or Nitinol or a combination thereof.

The object is further accomplished by the use of an implant as previously described for restoring a fractured bone.

The object is further accomplished by the use of an implant as previously described for preventing a fracture in a bone.

Fractured bones can for example be the humeral head or diaphysis, the calcaneus, the wrist radius, the tibia, the pelvis or the ribs. Examples for an application for preventing the fracture of the bone is e. g. the humerus or the ribs or spinal vertebral body for example in case of severe osteoporosis or lytic lesion tumour induced.

The object is further accomplished by a method of stabilizing a fractured or non-fractured bone by inserting a bone implant as previously described into a bone and preferably introducing bone cement into the bone through the bone implant.

Such a method leads to an easy introduction and fixation of the bone implant inside the bone without the need of any plates or additional fixation means.

BRIEF DESCRIPTION OF THE DRAWINGS

In the following, the invention is described in embodiments by means of figures. It shows:

FIG. 2: a first section of a bone implant in a second embodiment

FIG. 3: a cross-section through a bone implant in a third embodiment,

DESCRIPTION OF THE PREFERRED EMBODIMENTS

Figure 1:
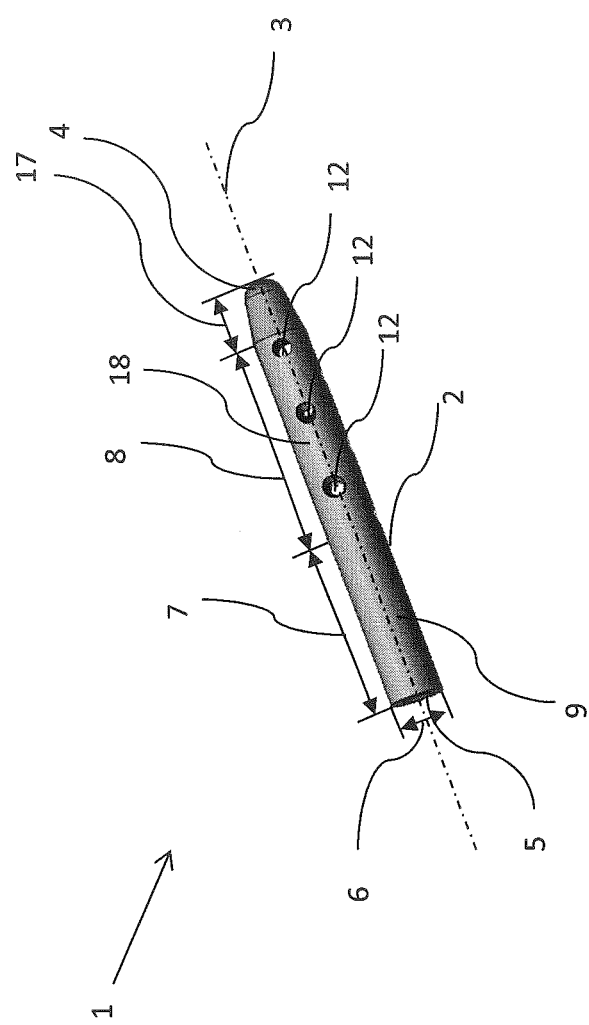
FIG. 1: a bone implant in a first embodiment.
Figure 5:
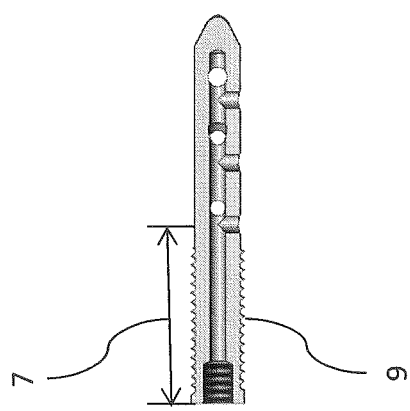
FIG. 5: a cross-section through a bone implant according to FIG. 4.

FIG. 1 shows a bone implant 1 according to a first embodiment. The bone implant 1 comprises an implant body 2 having a longitudinal axis 3. The implant body 2 comprises a front side 4 and an end side 5. Additionally, the implant body 2 is separated into a first surface 7 and a second surface 8. The first surface 7 comprises an anchorage area 9 for improving the anchorage of the implant in a bone. Perpendicular to the longitudinal axis, the implant body 2 comprises an implant width 6. The implant width 6 is constant along the first surface 7 and the second surface 8 and not exceeded at any other point of the implant 1. The second surface 8 comprises holes 12 and a bore 10 inside the implant body 2. The holes 12 enable the introduction of a fluid such as bone cement through the implant 1 into the bone and optimize the fixation of the implant 1 inside the bone due to growing bone tissue into the holes 12. The implant body 2 further comprises a third surface 17 which has a conical shape. The width of the implant is reduced in the third surface such that the introduction of the implant 1 into the bone is easier. The front side 4 of the implant body 2 is rounded such that it forms a semi-sphere to facilitate introduction of the implant 1 into the bone. The anchorage area 9 of the first surface 7 comprises a surface structure for improving the anchorage of the implant 1 inside the bone. The holes are distributed 360° around the circumference of the implant body 2, while the holes 12 are arranged in rows. The rows are offset relative to each other such that a first hole 12 of a first row 18 has a different distance from the front side 4 than a second hole 12 of a second neighbouring row (not shown). The length of an implant body is 100 mm while the implant width is 5 mm. The diameter of the holes 12 is 2.5 mm. The wall of the holes 12 has a cylindrical shape.

For example values for standard spinal implant will be: length from 50 to 85 mm, preferably mean 70 mm, diameter from 4 to 7 mm, preferably 5 mm, holes from 1 mm to 3 mm. preferably 2-2.5 mm.

FIG. 2 shows a cross-section through a second embodiment of the invention. In this embodiment, the implant body 2 comprises a bore 10 along the longitudinal axis. On the end side 5 a fixation connector is arranged to enable a connection of the implant body 2 with an insertion tool (not shown). Contrary to the first embodiment in FIG. 1, the holes 12 in the second embodiment are arranged over a larger second surface 8 relative to a smaller first surface 7. A first set of holes 12 comprises a hole axis 11a which is arranged perpendicular to the longitudinal axis 3. A second set of holes comprises an inclined axis 11b, while the inclination of the hole axis 11b is 120° relative to the longitudinal axis 3. The front side 4 further comprises a third surface 17 for facilitating introduction of the implant into a bone.

FIG. 3 shows a cross section of a third embodiment of the invention. In this embodiment the bore 10 comprises a fixation connector 16 on the end side 5 of the implant body 2 which is threaded. By means of this thread a tool can be fixed in the implant. The holes 12 are arranged 270° around the longitudinal axis 13 and hence a fluid such as bone cement is only directed 260° from the implant. This way, sensitive areas will not be filled with fluid or specific bone cement.

Figure 4:
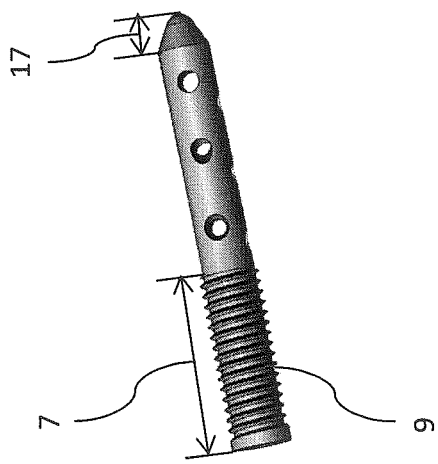
FIG. 4: a bone implant in a fourth embodiment.

FIG. 4 shows a fourth embodiment of the invention. This embodiment corresponds to the first embodiment in FIG. 1 apart from the first surface 7 comprising the anchorage area 9. The anchorage area 9 comprises a thread in which the thread pitches extend from the implant width 6. Such an anchorage area 9 improves the fixation of the implant inside the bone. Furthermore, the third surface 17 in this embodiment is shorter relative to the embodiment in FIG. 1 and thereby a conical shape of the third surface 17 comprises a steeper inclination relative to the embodiment in FIG. 1. Additionally, the front side 4 is more peaked relative to the embodiment in FIG. 1.

FIG. 2 shows the embodiment as disclosed in FIG. 3 while the first surface 7 comprises an anchorage area 9 having a thread. The anchorage area 9 in this embodiment corresponds to the anchorage area 9 shown in FIG. 4.

Figure 6A:
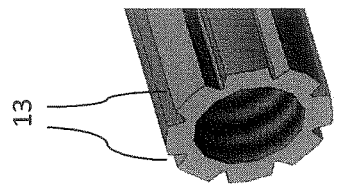
FIGS. 6a to 6c: a detailed view of FIG. 6.
Figure 6B:
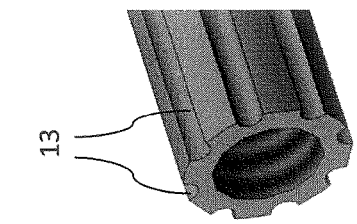
Figure 6C:
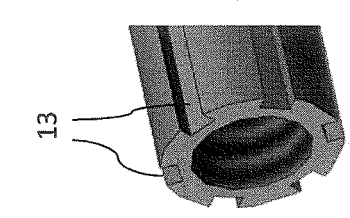
Figure 6:
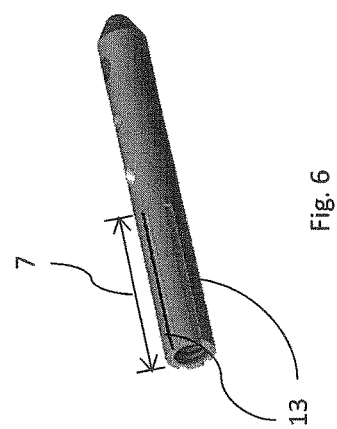
FIG. 6: a bone implant in a fifth embodiment.

FIG. 6 shows an embodiment of the implant 1 which comprises a first surface 7 having longitudinal grooves 13. The longitudinal 13 grooves improve the anchorage of the bone implant inside the bone. The longitudinal grooves can comprise a cross-sectional shape that is square, such that it avoids rotation (FIG. 6a), semi-spherical such that insertion is easier and the bone contact is better compared to square shapes or angles (FIG. 6b) or triangular such that the surface contact is maximised (FIG. 6c). The holes 12 in the embodiment according to FIG. 6 are only distributed from 270° up to 300° around the circumference of the implant 1.

Figure 7:
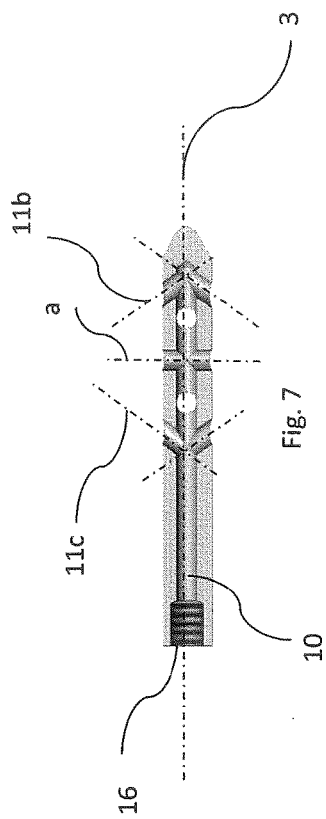
FIG. 7: a cross-section through a bone implant in a sixth embodiment

FIG. 7 shows a cross-section through the embodiment according to FIG. 6. The bore 10 along the longitudinal axis 3 comprises a fixation connector 16 which enables a threaded connection to a tool (not shown). The holes 12 are arranged along three different hole axis 11a to 11c. The first hole axis 11a is arranged perpendicular to the longitudinal axis. The hole axis 11b for the second set of holes is arranged at 130° relative to the longitudinal axis 3. The hole axis 11c for the third set of holes is arranged at 60° relative to the longitudinal axis. Such a hole arrangement is especially suitable for an implant in a vertebra since bone cement introduced through the bore 10 and holes 12 is optimally distributed in the vertebra. The purpose is to avoid the risk of leakage through the vertebral body walls, anterior or posterior, that could have been damaged by a fracture.

FIGS. 8a to 8c show an exemplary embodiment of the use of the implant in a vertebra. FIG. 8a shows the top view, FIG. 8b shows a side view and FIG. 8c shows a rear view from a vertebra in which two implants are introduced for stabilizing the vertebra. The implants introduced in this embodiment are implants according to FIG. 1.

Figure 8:
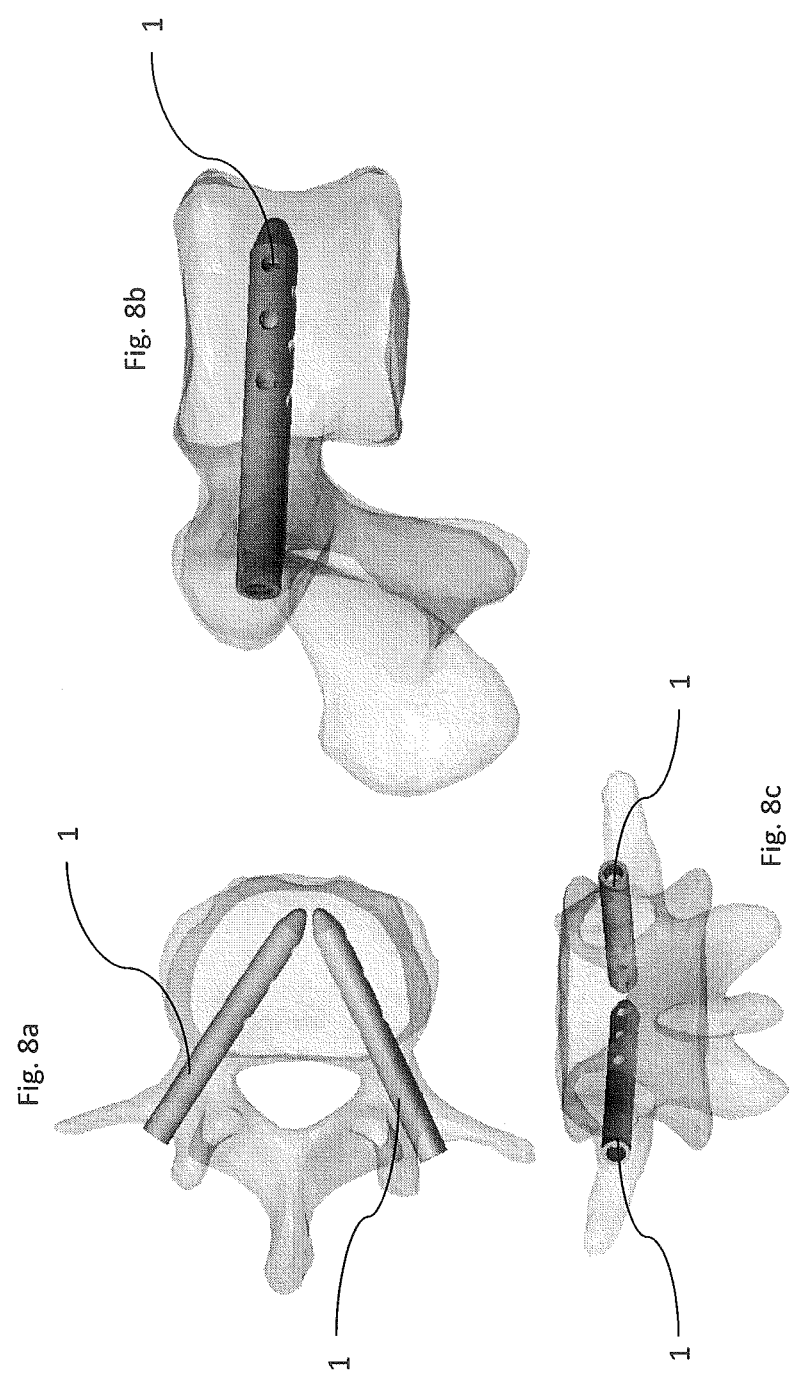
FIG. 8: two bone implants stabilizing a fracture in a vertebra.
Figure 9:
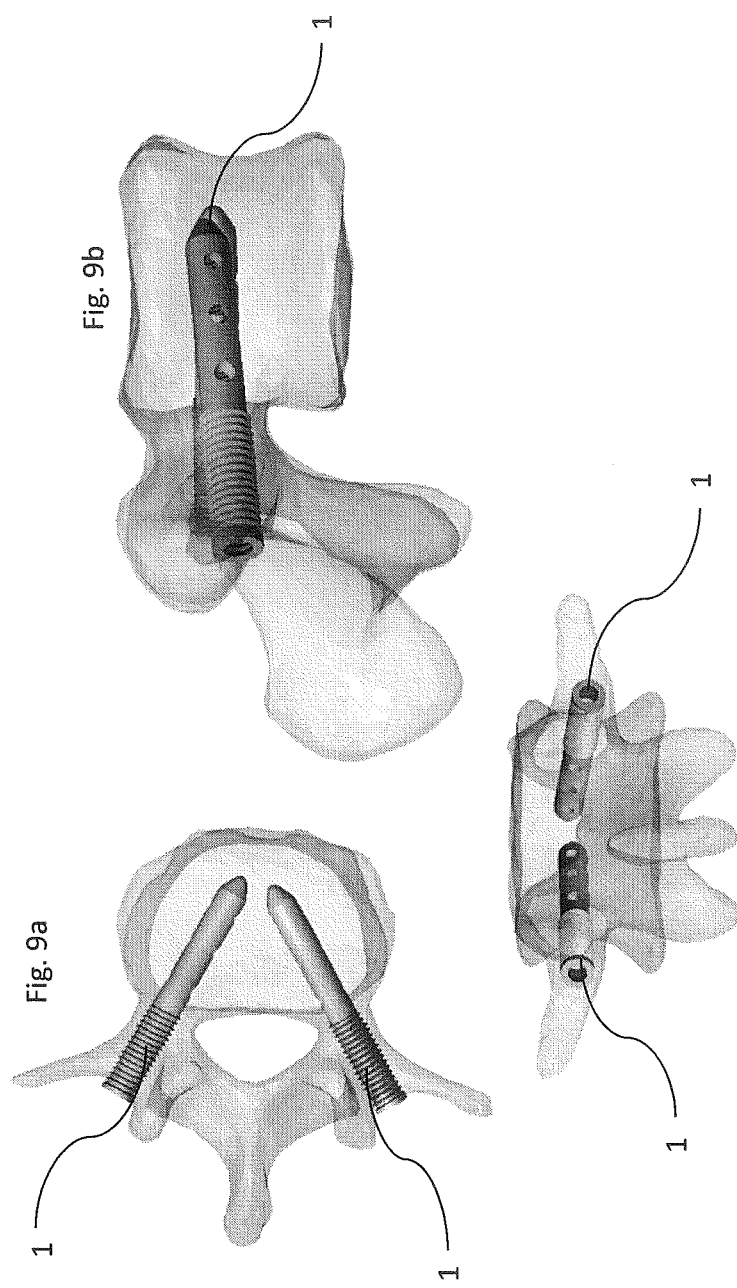
FIG. 9: two implants according to the third embodiment for stabilizing a fracture in a vertebra.

FIGS. 9a to 9c show the same views as FIG. 8 applying an embodiment of the implant according to FIG. 4.

Figure 10:
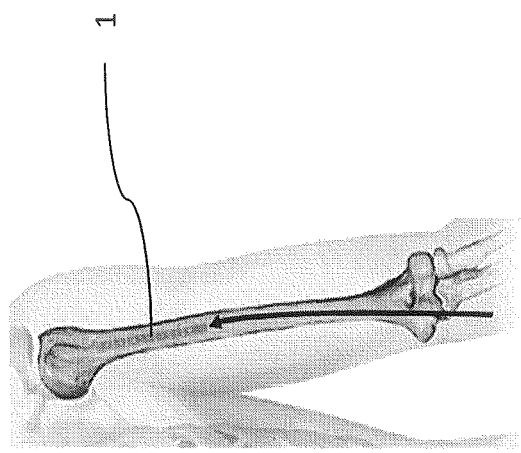
FIG. 10: a bone implant according to the first embodiment for stabilizing the humerus.

FIG. 10 shows an implant 1 used as a stabilizing implant in a humerus. The humerus is not fractured. The implant 1 is nevertheless introduced into the bone for stabilizing it. The arrow shows the way of introducing implant 1 into the humerus.

The invention claimed is:

1. A bone implant for stabilizing fractured or non-fractured bones, said implant comprising:
   an implant body extending along a longitudinal axis, from a front side to an end side, and having an implant width extending perpendicularly to the longitudinal axis,
   wherein a length of said implant body along said longitudinal axis is at least 5 times said implant width,
   said implant body has an outer surface which is divided at least into a first surface and a second surface, and
   said first surface comprises an anchorage area which extends at least partially over said outer surface but no greater than half of the outer surface,
   the implant does not have any widening at a proximal end thereof,
   holes are substantially equally distributed 360° around at least one of the outer surface or the second surface, the distributed holes form longitudinal rows of holes which extend along the longitudinal axis of the implant body such that a spacing between adjacent holes, located within the longitudinal row of holes, is substantially the same, wherein said holes are not connected by a groove.

2. The bone implant according to claim 1, wherein the implant comprises a bore extending along said longitudinal axis or parallel to said longitudinal axis having at least one opening at said front side and/or at said end side.

3. The bone implant according to claim 1, wherein the length of the bone implant is in a range from 10 mm to 250 mm.

4. The bone implant according to claim 1, wherein the width of the bone implant is in a range from 2 mm to 10 mm.

5. The bone implant according to claim 1, wherein said outer surface comprises holes having a wall around a hole axis.

6. The bone implant according to claim 5, wherein the implant (1) comprises a first set of holes, and said hole axis of said first set of holes is arranged substantially perpendicular to said longitudinal axis.

7. The bone implant according to claim 5, wherein the implant comprises a second set of holes, and said hole axis of said second set of holes is inclined relative to said longitudinal axis.

8. The bone implant according to claim 1, wherein said anchorage area comprises fixation improvement structure.

9. The bone implant according to claim 1, wherein said anchorage area comprises surface structures in a form of grooves, distributed substantially equally around said longitudinal axis, extending coaxially along said longitudinal axis.

10. The bone implant according to claim 1, wherein the anchorage area comprises surface structures in a form of thread or ring shaped grooves.

11. A method of stabilizing a fractured or non-fractured bone by inserting a bone implant according to claim 1 into bone.

12. A bone implant for stabilizing fractured or non-fractured bones, said implant comprising:
   an implant body extending along a longitudinal axis, from a front side to an end side, and having an implant width extending perpendicularly to the longitudinal axis,
   wherein a length of said implant body along said longitudinal axis is at least 5 times said implant width,
   said implant body has an outer surface which is divided at least into a first surface and a second surface, and
   said first surface comprising an anchorage area which extends at least partially over said outer surface
   the implant body has a constant width over at least the first and the second surfaces without any widening at a proximal end of the implant,
   holes are substantially equally distributed 360° around at least one of the outer surface or the second surface, the distributed holes form longitudinal rows of holes which extend along the longitudinal axis of the implant body such that a spacing between adjacent holes, located within the longitudinal row of holes, is substantially the same.

* * * * *